United States Patent [19]

Michalský, deceased et al.

[11] Patent Number: 5,597,831

[45] Date of Patent: Jan. 28, 1997

[54] 6-[X-(2-HYDROXYETHYL) AMINOALKYL]-5,11-DIOXO-5,6-DIHYDRO-11-H-INDENO[1,2-C]ISOQUINOLINES AND THEIR USE AS ANTINEOPLASTIC AGENTS

[75] Inventors: JiříMichalský, deceased, late of Olomouc, by Miluška Michalská, Jana Michalská, legal heirs; JiříHrbata, Olšany; JiříKřepelka, Praha; Milan Mêlka, Hradec Králové; Milan Miko, Bratislava; Milan Hrubý; Milan Ferenc, both of Olomouc; Eva Skácelová, Hněvotín; Irena Kejhová, Praha; Růžena Reichlová, Praha; Anna Kargerová, Praha; Jitka Šedivá, Praha; Alois Koloničný, Pardubice; Josef Urbanec, Hradec Kraálové, all of Czechoslovakia

[73] Assignee: VUFB a.s, Praha, Czechoslovakia

[21] Appl. No.: 533,859

[22] Filed: Sep. 26, 1995

Related U.S. Application Data

[63] Continuation of Ser. No. 199,153, Jul. 13, 1994, abandoned.

[30] Foreign Application Priority Data

Aug. 29, 1991 [CS] Czechoslovakia ............. 2669-91

[51] Int. Cl.$^6$ .................. C07D 221/18; A61K 31/47
[52] U.S. Cl. ................. 514/284; 546/61; 424/573
[58] Field of Search ................ 546/61; 514/284

[56] References Cited

PUBLICATIONS

Wawzonek et al, The Journal of Organic Chemistry, vol. 33(2) pp.–896–897 Feb. 1968.
Cushman et al., Journal of Medicinal Chemistry, vol. 27(4) pp.–544–547 (1984).

Primary Examiner—Alan L. Rotman
Attorney, Agent, or Firm—Burns, Doane, Swecker & Mathis, L.L.P.

[57] ABSTRACT

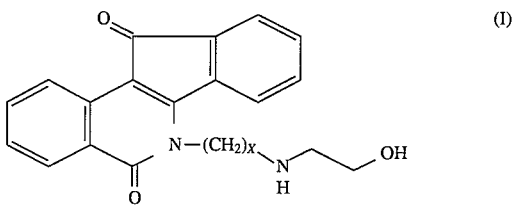

New 6-[X-(2-hydroxyethyl)aminoalkyl]-5,11-dioxo-5,6-dihydro-11H-indeno[-1,2-c]isochinoline derivatives represented by general formula (I), in which X stands for the number of carbon atoms from 0 to 5 in aminoalkyl group situated on nitrogen atom in position 6 of the indenoisochinoline fundamental structure, their salts with inorganic and organic acids and their derivatives were described. Antitumorously effective indenoisochinoline derivatives are most preferably prepared by the process in which the indeno[1,2-c]isocoumarine and/or 1-methoxy-2-(2-methoxycarbonylphenyl)-1-inden-3-one, respectively, comprises reacting with N-(hydroxyethyl)alkylen diamine in a medium of suitable aprotic solvent, preferably dimethylformamide, and at increased temperature. Another process for the preparation comprises reacting 6-(X-chloroalkyl)-5,11-dioxo-5,6-dihydro-11H-indeno[1,2-c]isochinolines with 2-aminoethanol in suitable solvent, preferably dimethylformamide, in the presence of anhydrous potassium carbonate. New compounds, their derivatives and salts are useful for the preparation of drugs and compositions for the treatment of malignant neoplasias in mammals.

5 Claims, 1 Drawing Sheet

6-[X-(2-HYDROXYETHYL) AMINOALKYL]-5,11-DIOXO-5,6-DIHYDRO-11-H-INDENO[1,2-C]ISOQUINOLINES AND THEIR USE AS ANTINEOPLASTIC AGENTS

CONTINUING DATA

This application is a continuation of application Ser. No. 08/199,153, filed Jul. 13, 1994, abandoned, which is a 371 of PCT/US 92/0026 filed Aug. 27, 1992.

TECHNICAL FIELD

The invention relates to 6-[X-(2-hydroxyethyl)aminoalkyl]-5,11-dioxo-5,6-dihydro-11H-indeno[1,2-c]isoquinolines of the general formula I

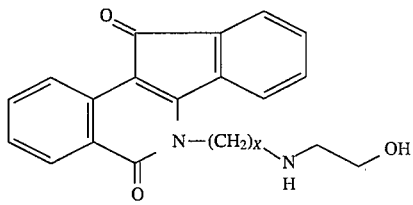

in which X stands for the number of carbon atoms from 0 to 5 in aminoalkyl group situated on nitrogen atom in position 6 of the indenoisoquinoline fundamental structure, their salts with inorganic and organic acids, and to a process of the preparation thereof.

The subject compounds of general formula I (e.g. bases of compounds of general formula I) and their salts with pharmaceutically and pharmacologically acceptable acids, respectively, have usable antineoplastic activity and can be used in monotherapy and/or in combination with other antineoplastic drugs in the treatment of suitable biological subjects, especially of mammalian origin.

BRIEF DESCRIPTION OF THE INVENTION

New 6-[X- (2-hydroxyethyl)aminoalkyl]-5,11-dioxo-5,6-dihydro-11H- indeno[1,2-c]isoquinolines represented by the general formula I

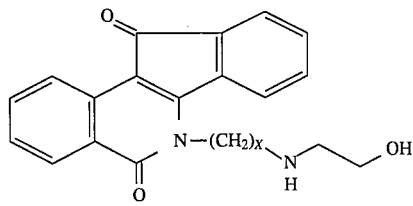

in which X stands for the number of carbon atoms from 0 to 5 in aminoalkyl group situated on nitrogen atom in position 6 of the indenoisoquinoline fundamental structure and their salts with inorganic and organic acids were described.

Antitumorously effective indenoisoquinolines are most preferably prepared by the process in which the indeno[1,2-c]isocoumarine and/or 1-methoxy-2-(2-methoxycarbonylphenyl)-1-inden-3-one, respectively, comprises reacting with N-(hydroxyethyl)alkylen diamine in a medium of suitable aprotic solvent, preferably dimethylformamide, and at increased temperature. Another process for the preparation comprises reacting 6-(X-chloroalkyl)-5,11-dioxo-5,6-dihydro-11H-indeno[1,2-c]isoquinolines with 2-aminoethanol in suitable solvent, preferably dimethylformamide, in the presence of anhydrous potassium carbonate.

New compounds, and their salts are useful for the preparation of drugs and compositions for the treatment of malignant neoplasias in mammals.

BACKGROUND ART

The pertinent literature reports certain indeno[1,2-c]isoquinoline derivatives as products of degradation of alkaloid cryptopine [Perkin, W. H.: J. Chem. Sec. 109, 815 (1916); ibid. 115, 713 (1919); Dyke, S. F., Brown, D. W.: Tetrahedron 24, 1455 (1968)]. 11-H-indeno[1,2-c]isoquinoline and/or 5-hydroxy-11H-indeno[1,2-c]isoquinoline-N-oxide were prepared by reacting 11H-indeno[1,2-c]isocoumarine with ethanolic ammonia and/or hydroxylamine, respectively [Chatterjea, J. N., Mukherjee, H.: J. Indian Chem. Sec. 37, 379 (1960)].

5,11-dioxo-5,6-dihydro-11H-indeno[1,2-c]isoquinoline formed by reacting of 11-oxo-11H-indeno[1,2-c]isocoumarine with ethanolic ammonia under high pressure was described [Wawzonek, S., Stowell, J. K., Karll, R. E.: J. Org. Chem. 31, 1004 (1966)].

Indenoisoquinoline analogues of highly toxic nitidine and fagaronine have been also prepared [Cushman, H., Mohan, P., Smith, E. C. R.: J. Med. Chem. 27, 544 (1984); Cushman, M., Mohan, P.: J. Med. Chem. 28,1031 (1985)].

The named indenoisoquinoline compounds did not exhibit any useful biological activity with the exception of indenoisoquinoline analogues of fagaronine and nitidine which showed a weak antineoplastic action.

According to our knowledge, compounds of the present invention, 6-[X-(2-hydroxyethyl)aminoalkyl]-5,11-dioxo-5,6-dihydro-11H-indeno[1,2-c]isoquinolines of the general formula in which X stands for a number of carbon atoms from 0 to 5 in aminoalkyl group situated on nitrogen atom at position 6 of the indenoisoquinoline fundamental structure (eg bases of compounds of general formula I) and their salts with pharmaceutically and pharmaceutically acceptable acids, respectively, represent a new previously undescribed class of compounds which surprisingly showed a remarkable antineoplastic activities "in vitro" and "in vivo" which have not been described yet. The main advantage of new compounds is a great efficacy even after oral administration, low toxicity and in comparison with intercalating agents (antibiotics) synthetic attainability.

DISCLOSURE OF INVENTION

As a result of extensive investigation, it has been found, that novel 6-[X-(2-hydroxyethyl)aminoalkyl]-5,11-dioxo-5,6-dihydro-11H-indeno[1,2-c]isoquinolines of the general formula I in which X stands for the number of carbon atoms from 0 to 5 in aminoalkyl group situated on nitrogen atom in position 6 of the indenoisoquinoline fundamental structure and their salts with inorganic and organic acids and have usable antineoplastic activity and can be used in monotherapy and/or in combination with other antineoplastic drugs in the treatment of suitable biological subjects, especially of mammalian origin.

There are three procedures usable to prepare indeno-[1,2-c]isoquinolines of the general formula I and all of them have a conventional character.

As starting substances were used:
1. Easily attainable 11-oxo-11H-indeno[1,2-c]isocoumarine (II) [cf. Pailer, M., Worther, H., Meller, A.: Mh. Chem. 92, 1037 (1961)], 2. 1-methoxy-2-(2-methoxycarbonylphenyl)-1-inden-3-one (III) [Pailer, M., et al.: 1. c.] and
3. 6-(X-chloroalkyl)-5,11-dioxo-5,6-dihydro-11H-indeno-[1,2-c]isoquinolines (IV).

Indeno[1,2-c]isoquinolines of the general formula I (X=0 to 5) are preferably obtained by the condensation from indeno[1,2-c]isocoumarine (II) and/or 1-methoxy-2-(2-methoxycarbonylphenyl)-1-inden-3-one (III) respectively, with N-(hydroxyethyl)alkylendiamine, with a number of carbon atoms in alkyl chain from 0 to 5, in hot dimethylformamide. The next common process of preparation of the compounds of type I is a condensation with 6-(X-chloroalkyl)-5,11-dioxo5,6-dihydro-11H-indeno[1,2-c]isoquinolines of type IV with etanolamine in dimethylformamide in the presence of anhydrous potassium carbonate.

cal subject and increasing the number or the growth of tumour cells. Tumour growth may be observed clinically or in experiments in vivo, that is, with experimental animals, or in vitro, for example, in tissue cultures prepared from tumours. The assessment of tumour growth may be effected by measuring the weight of the tumour mass, or, more effectively, by measuring the radioactivity after incorporation therein of certain substances of natural origin such as amino acids (for example, valine, leucine, natural amino-acid mixture), nucleic bases (e.g. adenine), nucleosides (thymidine, uridine), their analogs (5-iododeoxyuridine) etc., labelled with radioactive atoms such as 14C, 3H, etc. Such a useful therapeutical effect of the compounds of the present invention has been proven in experiments with ascites form of sarcoma 37 (37), adenocarcinoma HE and/or solid form of Ehrlich tumour after oral and parenteral

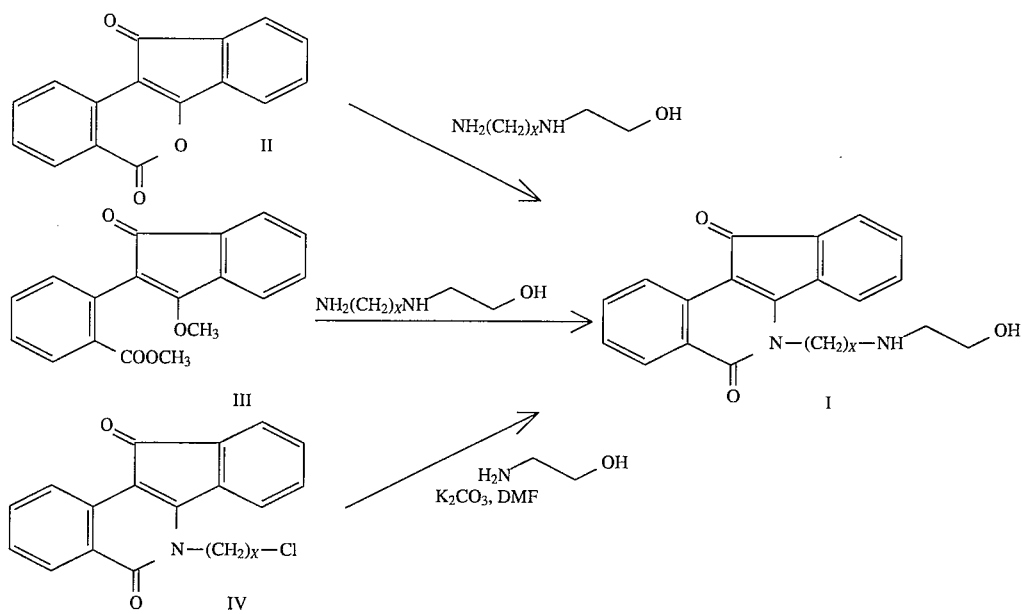

The antineoplastic activity of the compounds of the invention has been investigated testing the compounds of the chemical group "in vivo" against experimental rodent tumors such as the solid form of Ehrlich tumour (STE, originally mammary adenocarcinoma), tumor HK (also transplantable originally mammary adenocarcinoma), Krebs' ascites tumour (Kr2), S37 ascites sarcoma, Nemeth-Keller lymphoma (NK), all maintained in mice H, Gardner lymphosarcoma (LsG, maintained in mice C3H), P388 and/or L1210 leukemia (maintained in DBA2mice), B16 metastasizing melanocarcinoma (maintained in C57B⅙ mice) and Yoshida ascites reticulosarcoma (Y, maintained in Vistar rats) in experiments according to Jelinek, V. [Neoplasma 12, 469 (1965); ibid 7, 146 (1960)] and in "in vitro" experiments using radioactive precursors of nucleic acids and proteins according to Miko, M. et al. [Cancer Res 39, 4242 (1979); Neoplasma 26, 449 (1979); ibid 16, 161 (1969)] with minor modifications [Mattern, J.: Studies on the Drug Sensitivity of Short Term Cultured Tumour Cell Suspensions. In "Human Tumours in Short Term Cultured" (Dendy, P. P. ed.), p.301, Academic Press 1976]. The Cox's proportional-hazards model was used for survival evaluation and optimal dose calculation according to Carter, V. H. et al. [cf Cancer Res. 42, 2963 (1982)].

The therapeutic effect for the purposes of the invention means the inhibition of characteristic disease symptoms in biological subjects bearing tumours which are especially tumour growth, shortening of the survival period of biologiadministration of the compounds of the chemical group. By comparison with untreated control animals, significantly lower mean tumour weights have been observed in treated groups of animals (of examples). Additionally, the compounds of the invention are useful in increasing survival time of the suitable biological subjects, especially mice and rats bearing tumors S37, HK, STE, LsG and Y, and/or leukemias P388 and L1210, especially after oral administration; because the lethal nature of the test system employed, the antitumor effect of the compounds is illustrated by a side-by-side comparison of the survival time of treated animals (those which survived for a longer time) with the untreated control groups of animals. In the typical experiments (cf examples) ten animals were in the experimental groups and the treated groups of animals survived for a longer time than the uncreated controls. After in, ravenous administration of 6-[2-(2-hydroxyethyl)aminoethyl]-5,11-dioxo-5,6-dihydro-11H-indeno[1,2-c]isoquinoline hydrochloride, a typical compound of the chemical group, the highly significant increase of survival of mice DBA2 with leukemia P388 has been proven. The compounds and their salts revealed direct cytotoxicity against tumor cells of Yoshida, Ehrlich and Gardner tumors and leukemia L1210 and its resistant variant developed after treatment with mitoxantron. The compounds of the present invention are also potent inhibitors of DNA, RNA and protein biosyntheses of the tumor cells. This conclusion clearly followed from examples. Inhibition of any of the vital biosynthesis mentioned above is attainable as a result of antitumor activity of cytostatic drugs. The compounds described herein can be administered to suitable biological subjects, particularly mammals, for their therapeutic antitumor effects by conventional modes of administration alone, but preferably as active ingredients with any conventional suitable non-toxic pharmaceutical carrier, dissolved or suspended, for example, in water, saline, polyethylene or polypropylene alcohols, etc. The administration is preferably by the oral route. The dosage administered will be dependent upon the type of tumor for which treatment is desired, the type of biological subject involved, weight, body surface, localisation of the tumor, its morphological type, the frequency of treatment, ere; biological test revealed that the tolerable oral dose was up to 400 mg/kg (1200 mg/m$^2$). ED 95 was 225 mg/kg p.o. (675 mg/m$^2$) of the base of typical compound in L1210 bearing mice DBA2. Intravenous doses represent about half of those in oral administration, as well as repeated doses in oral administration prolonged for five days. The compounds have low toxicity, the LD 50 value in mice is about 700 mg/kg p.o.

It is evident that therapeutically useful effects can be expected to occur upon the administration of such doses that are completely non-toxic to the respective mammalian organism. The conclusion follows from biological tests that single oral dose of 675 mg/m$^2$ is expected to be tolerable and effective in man.

MODES OF CARRYING OUT THE EXAMPLES

Figure 1:
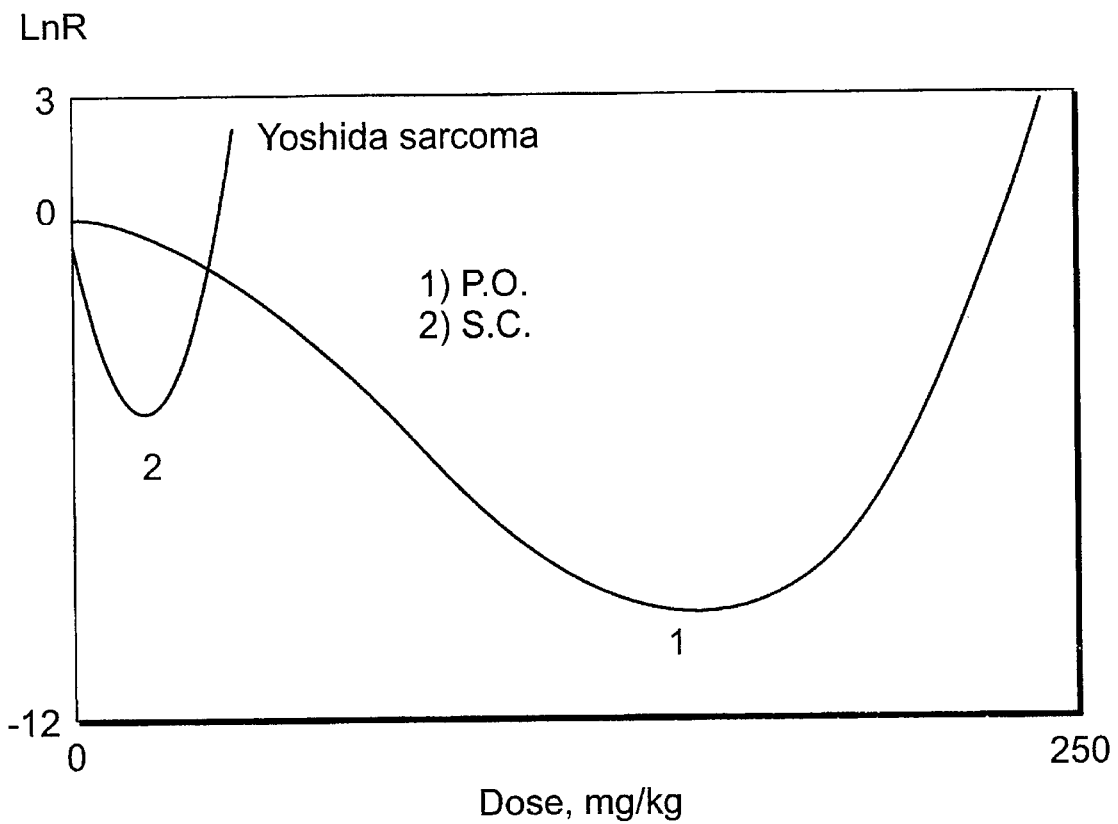
FIG. 1 shows dose-response curves for the typical compound of the formula I wherein X=2 (see Example 8) in Yoshida ascites tumour bearing rats.

The process for preparing the subject compounds of formula I as well as selected results of their biological studies are illustrated by The following non-limitative examples. Melting points were determined on Kofler block and are not corrected, yields are indicated in stoichiometric of theory.

EXAMPLE 1

6-[2-(2-hydroxyethyl)aminoethyl]-5,11-dioxo-5,6-dihydro-11H-indeno[1,2-c]isoquinoline (I; X=2)

A suspension of 5 g 11-oxo-11H-indeno-[1,2-c]isocoumarine (II, m.p. 258° C.) in 60 ml of dimethylformamide is treated by addition of 3 g of N-(2-hydroxyethyl)ethylendiamine all at once and the mixture is stirred warming to 110° C. After an hour heating the clear red solution is cooled to laboratory temperature and the precipitated product is separated by suction after twelve hours of standing, washed with 60 ml of ethanol and dried at a temperature of 60° C. to yield 6.0 g (89%) of the product melting at 184° C. The purification of the title indenoisoquinoline (I; X=2) is carried out by crystallization from a mixture of dimethylformamide and ethanol. The compound produces small orange needles melting at 184° C.

EXAMPLE 2

6-[3-(2-hydroxyethyl)aminopropyl]-5,11-dioxo-5,6-dihydro-11H-indeno[1,2-c]isoquinoline (I; X=3)

At the same conditions (see example 1) the condensation of 5.9 g of 1-methoxy-2-(2-methoxycarbonylphenyl)-1-inden-3-one (III, m.p. 116°–118° C.) with 2-(3aminopropylamino)ethanol in 60 ml of dimethylformamide is carried out at 110° C.

After the reaction has come to an end, 70 ml of distilled water was added to hot solution in parts. The mixture was cooled to the temperature of 3°–5° C., the precipitated red-orange crystallic substance was separated by suction after twenty hours of standing, washed with water (100 ml) and after drying at a temperature of 60° C.(m.p. 151°–153° C., yield 5.35 g, e.g. 80%) recrystallized from ethanol. The product melts at 155° C.

EXAMPLE 3

6-[2-(2-hydroxyethyl)aminoethyl]-5,11-dioxo-5,6-dihydro-11H-indeno[1,2-c]isoquinoline (I; X=2)

A mixture of 1 g of 6-(2-chloroethyl)-5,11-dioxo-5,6-dihydro-11H-indeno[1,2-c]isoquinoline (IV, X=2, m.p. 214°–215° C.), 1 g of dry 2-aminoethanol and 1 g of anhydrous potassium carbonate in 30 ml of anhydrous dimethylformamide is treated by warming to 100°14 110° C. and kept at this temperature for two hours. The hot mixture is filtered and the product collected on filter washed with 10 ml of ethanol. After twelve hours of standing in refrigerator (5° C. the eliminated crystallic substance is separated by suction, washed with ethanol and dried at temperature of 60° C. The yield 0.7 g (65% of theory), m. p. of the product is 184° C. It is possible to purify the substance as in Example 1.

EXAMPLE 4

6-[2-(2-hydroxyethyl)aminoethyl]-5,11-dioxo-5,6-dihydro-11H-indeno[1,2-c]isoquinoline hydrochloride (I; X=2)

To 120 ml of distilled water warmed to the temperature of 75°–80° C. 6 g of the base of the substance I (X=2) is added and after brief stirring the mixture is treated by 30 ml of concentrated hydrochloric acid. After 5 minutes of stirring 300 ml of ethanol warmed of the temperature of 50°–60° C. are added. The suspension is refluxed for 10 minutes and after dissolving filtered promptly and left to crystallize at the temperature of 20° C. for 20 hours. The yield is 6.1 g (91% of theory).

EXAMPLE 5

An illustration of the antitumour activity of 6-[2-(2-hydroxyethyl)aminoethyl]-5,11-dioxo-5,6-dihydro-11H-indeno[1,2-c]isoquinoline (the substance I, X=2) in mice after oral administration of the drug.

Eighty female mice H weighing approximately 20 g were divided into four groups: one control group and three experimental groups of 20 animal each. A lethal dose of the Sa37 sarcoma ascitic fluid was implanted intraperitoneally to all the animals. The animals of test groups were treated using the compound suspended in water. The suspension contained the substance in such a concentration that dose 0.6, 0.4 and/or 0.2 ml of the suspension p.o. was equal to dose 240, 160 and/or 80 mg/kg p.o., respectively. The drug was administered to the experimental animals once, a day after tumour transplantation. On the tenth day after the tumour transplantation, half of she animals in each group were killed by ether anaesthesia, ascites were emptied after laparotomia and the tumour weight was assessed in all animals from the weight difference before and after laparotomia and ascites removing. In ascites fluid the volume of tumour cell fraction was determined. The remaining animals were left to monitor the time of death and survival time was followed. Statistically, significantly lower mean values of the tumour weight as well as mean values of tumour cell fraction in ascites fluid (e.g. total ascitocrit) were observed in the treated animals in comparison with the untreated control group (Student's t-test, $p<0.001$). It was also observed that the treated animals survived longer than untreated control animals. The mean survival time values of treated groups were significantly (Student's t-test, p<0.01) higher in comparison with that one of the untreated control group of animals. The results of the experiment are summarized in the following table:

Antitumour activity of 6-[2-(2-hydroxyethyl)aminoethyl]-5,11-dioxo-5,6-dihydro-11H-indeno[1,2-c]isoquinoline (the substance I, X = 2) in S37 sarcoma bearing mice.

| Substance | Dose (mg/kg) p.o. | Tumour weight (T/C, %) | Survival time (T/C, %) | Total ascitocrit (T/C, %) |
|---|---|---|---|---|
| I | 240 | 42[c] | 119[b] | 47[c] |
| (X = 2) | 160 | 59[c] | 111 | 65[c] |
|  | 80 | 61[c] | 107 | 64[c] |

[b] p = 0,01
[c] p = 0,001

EXAMPLE 6

An illustration of the antitumour activity of 6-[2-(2-hydroxyethyl)aminoethyl]-5,11-dioxo-5,6-dihydro-11H-indeno[1,2-c]isoquinoline (the substance I, X=2) and 6-[3-(2-hydroxyethyl)aminopropyl]-5,11-dioxo-5,6-dihydro-11H-indeno[1,2-c]isoquinoline (the substance I, X=3) in mice after oral administration of the drug.

In an analogous experiment carried out on the animals with implanted Sa37 sarcoma the substance I (X=2) was administered in seven daily doses, and the substance I (X=3) in four days. The results of the experiment are summarized in the following table:

Antitumour activity of 6-[2-(2-hydroxyethyl)aminoethyl]-5,11-dioxo-5,6-dihydro-11H-indeno[1,2-c]isoquinoline (the substance I, X = 2) and 6-[3-(2-hydroxyethyl)aminopropyl]-5,11-dioxo-5,6-dihydro-11H-indeno[1,2-c]isoquinoline (the substance I, X = 3) in S37 bearing mice.

| Substance | Dose (mg/kg) p.o. | Tumour weight (T/C, %) | Survival time (T/C, %) | Total ascitocrit (T/C, %) |
|---|---|---|---|---|
| I | 30 | 32[b] | 86 | 40[b] |
| (X = 2) | 20 | 64[b] | 129[a] | 73[a] |
|  | 10 | 66[b] | 129 | 73[b] |
| I | 30 | 35[b] | tox | 43[b] |
| (X = 3) | 20 | 56[c] | 99 | 62[c] |
|  | 10 | 70[b] | 119 | 80[a] |

[a] p < 0,05
[b] p < 0,01
[c] p < 0,001
tox — toxic dose

EXAMPLE 7

An illustration of the antitumour activity of 6-[2-(2-hydroxyethyl)aminoethyl]-8, 11-dioxo-8, 6-dihydro-11H-indeno[1,2-c]isoquinoline (the substance I, X=2) in mice after oral administration of the drug.

Sixty female mice H weighing approximately 20 g were divided into three groups: one control group and two experimental groups of 20 animal each. A lethal dose of the 40 Ehrlich tumour homogenate was implanted subcutaneously to all the animals. The animals of test groups were treated using the compounds suspended in water. The suspension contained the substance in such a concentration that dose 0.4 and/or 0.2 ml of the suspension p.o. was equal to dose 400 and/or 200 mg/kg p.o., respectively. The drug was administered to the experimental animals once, the fifth day after tumour transplantation. On the fourteenth day after the tumour transplantation, half of the animals in each group were killed by ether anaesthesia, tumours were removed and weighed. The remaining animals were left to monitor the time of death and survival time was followed. Statistically, significantly lower wet mean values of the tumour weight were observed in the treated animals in comparison with the untreated control group (Student's t-test, p<0.01). It was also observed that the treated animals survived longer than untreated control animals. The mean survival time values of treated groups were significantly (Student's t-test, p<0.05) higher in comparison with that one of untreated control group of animals. The results of the experiment are summarized in the following table:

| Substance | Dose (mg/kg) p.o. | Tumour weigt (T/C, %) | Survival time (T/C, %) |
|---|---|---|---|
| I | 400 | 31[b] | 152[a] |
| (X = 2) | 200 | 79[a] | 111 |

[a] p = 0,05)
[b] p = 0,01

EXAMPLE 8

An illustration of the antitumour activity of 6-[2-(2-hydroxyethyl)aminoethyl]-5,11-dioxo-5,6-dihydro-11H-indeno[1,2-c]isoquinoline (the substance I, X=2) in rats after oral and parenteral administration of the drug.

Seventy infantile Vistar female rats weighing 63.0–64.8 g were divided into seven groups: one control group and six experimental groups of 10 animal each. A lethal dose of the Yoshida reticulosarcoma ascitic fluid was implanted intraperitoneally To all The animals. The animals of Test groups were Treated using The compound suspended in water. The suspension contained The substance in such a concentration that dose. 0.6, 0.4 and/or 0.2 ml of the suspension was equal To dose 200, 100 and/or 50 mg/kg p.o., or 40, 20 and/or 10 mg/kg s.c., respectively. Doses of The drug were administered to The experimental animals once a day, for five consecutive days, starting on the first day after tumour transplantation. In all animals survival was followed. It was observed that the treated animals survived longer than untreated control animals. The mean survival time values of treated groups were significantly (Student's t-test, p<0.01) higher in comparison with that one of untreated control group of animals. The results of the experiment are summarized in the following table and shown in the graph on the FIG. 1.

| Substance | Administration | Dose (mg/kg) | Period of[f] survival (% of control) |
|---|---|---|---|
| I | p.o. | 200 | 219[b,d] |
| (X = 2) |  | 100 | 230[b,e] |
|  |  | 50 | 132 |
|  | s.c. | 40 | 86 |
|  |  | 20 | 139[a] |
|  |  | 10 | 203[b] |

[a] p = 0,05
[b] p = 0,01
[d] 3 LTS (Long term survivors)
[e] 1 LTS
[f] T/C, %

EXAMPLE 9

An illustration of the antitumour activity of 6-[(2-hydroxyethyl)amino]-5,11-dioxo-5,6-dihydro-11H-indeno[1, 2c]isoquinoline (the substance I, X=0) in mice.

In an experiment carried out on the animals with implanted Sa37 sarcoma the substance I (X=0) was administered in eight daily doses (analogously as in example 6). Statistically, significantly lower mean value of the tumour weight as well as mean value of tumour cell fraction in ascites fluid (e.g. total ascitocrit) were observed in the treated animals after doses of 50 mg/kg p.o. (60 and 68%, respectively) and/or 20 mg/kg s.c. (68 and 71%, respectively) in comparison with the untreated control group (Student's t-test, p<0.01).

EXAMPLE 10

An illustration of the antitumour activity of 6-[(2-hydroxyethyl)amino]-5,11-dioxo-5,6-dihydro-11H-indeno[1,2-c]isoquinoline (the substance I, X=0) in mice after oral administration of the drug.

In experiment with Ehrlich tumour (solid form, see example 7) the drug administered to the experimental animals once at the single dose of 100 mg/kg p.o. significantly lowered the mean tumour weight (72% in the treated animals in comparison with the untreated control group). The drug administered eight times, starting on the first day after tumour transplantation, lowered mean tumour weight by 13%, significantly (p<0.05), at the doses of 50 mg/kg p.o. ×8. Mean survival time was higher (115%, p<0.05), in comparison with the untreated control group, after administration of eight daily doses of 25 mg/kg p.o.

EXAMPLE 11

Cytotoxicity of a salt of the substance I (X=2) in comparison with clinically useful drugs.

The degree of influence on the incorporation of [$^3$H] thymidine and [$^{14}$C]uridine into the fraction of Yoshida ascites cells insoluble in trichloroacetic acid serves as the measure of cytotoxicity. The IC50 value is the concentration of a cytostatic that reduces the $^3$H and $^{14}$C. incorporation down to 50% of the non-influenced control cells. The experimental results are summarized in the following table.

| Effect of the hydrochloride of the substance I (X = 2) on Yoshida ascites tumor cells. | | | |
|---|---|---|---|
| Substance | MW | Precursor | IC50 (µmol.l$^{-1}$) |
| I (n = 2) Hydrochloride | 370.9 | [6-$^3$H]Thymidine | 5 |
| | | [Uracil-U-$^{14}$C]uridine | 7 |
| DOXORUBICIN | 548.0 | [6-$^3$H]Thymidine | 16 |
| | | [Uracil-U-$^{14}$C]uridine | 8 |
| MITOXANTRON | 517.4 | [6-$^3$H]Thymidine | 25 |
| | | [Uracil-U-$^{14}$C]uridine | 23 |

EXAMPLE 12

Cytotoxicity of the substance I (X=2) in vitro against L1210 leukemia cells and its variant L1210/MX developed for resistance to mitoxantron.

In analogous experiments to those already described the degree of influence on the incorporation of [$^{14}$C]amino-acid mixture into the L1210 leukemia cells and/or those of L1210/MX, a fraction insoluble in trichloroacetic acid serves as the measure of cross-resistance between the substance I (X=2) and mitoxantron. The experimental results are summarized in the following table.

| Substance | Tumor | Precursor | IC50 (µmol.l$^{-1}$) |
|---|---|---|---|
| I (X = 2) Base | L1210 | [U-$^{14}$C]Amino-acid mixture | 78 |
| I (X = 2) Base | L1210/MX | [U-$^{14}$C]Amino-acid mixture | 119 |

From the results it is evident that the cross-resistance is partial only. The substances of the patent application may be clinically useful in cases of tumour resistance against mitoxantron.

We claim:

1. 6-[X-(2-hydroxyethyl)aminoalkyl]-5,11-dioxo-5,6-dihydro-11H-indeno[1,2-c]isoquinolines of the formula I

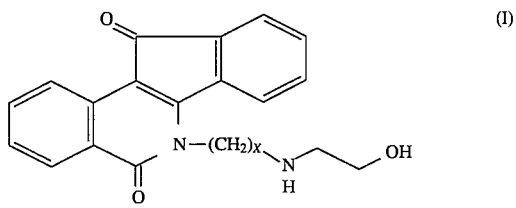

wherein X is a number from 0 to 5, or a pharmaceutically acceptable inorganic or organic acid addition salt thereof.

2. A pharmaceutical composition of matter for treatment of solid and ascites tumours, lymphomas and leukemias comprising a compound according to claim 1 in an amount effective for treatment of said solid and ascites tumours, lymphomas and leukemias, and a pharmaceutically acceptable carrier, excipient or diluent therefor.

3. A method for treating solid and turnouts selected from Sa37-sarcoma, Yoshida reticulosarcoma, Ehrlich tumour, Gardner lymphosarcoma, L1210-leukemia and P-388-leukemia in mammals comprising administering to a mammal a compound according to claim 1 in an amount effective for treatment of said solid and ascites tumours, lymphomas and leukemias.

4. The method according to claim 3, wherein solid and ascites tumours, lymphomas and leukemias represent Sa37-sarcoma, Yoshida reticulosarcoma, Ehrlich tumour, Gardner lymphosarcoma, L-1210-leukemia or P-388-leukemia.

5. The compound according to claim 1, wherein X is 2.

* * * * *